United States Patent
Vija et al.

(10) Patent No.: US 11,495,346 B2
(45) Date of Patent: Nov. 8, 2022

(54) EXTERNAL DEVICE-ENABLED IMAGING SUPPORT

(71) Applicant: Siemens Medical Solutions USA, Inc., Malvern, PA (US)

(72) Inventors: Alexander Hans Vija, Evanston, IL (US); Francesc dAssis Massanes Basi, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 79 days.

(21) Appl. No.: 16/948,220

(22) Filed: Sep. 9, 2020

(65) Prior Publication Data

US 2022/0076808 A1   Mar. 10, 2022

(51) Int. Cl.
*G16H 30/40*   (2018.01)
*G06T 7/00*   (2017.01)

(52) U.S. Cl.
CPC ........... *G16H 30/40* (2018.01); *G06T 7/0014* (2013.01); *G06T 2207/10016* (2013.01); *G06T 2207/10024* (2013.01); *G06T 2207/10028* (2013.01); *G06T 2207/20081* (2013.01); *G06T 2207/20101* (2013.01); *G06T 2207/30196* (2013.01)

(58) Field of Classification Search
CPC .................. G16H 30/40; G06T 7/0014; G06T 2207/10016; G06T 2207/10024; G06T 2207/10028; G06T 2207/20081; G06T 2207/20101; G06T 2207/30196
See application file for complete search history.

(56) References Cited

U.S. PATENT DOCUMENTS

| | | | |
|---|---|---|---|
| 9,940,753 B1* | 4/2018 | Grundhöfer et al. | G06T 19/006 |
| 11,200,689 B1* | 12/2021 | Smith | G06N 20/10 |
| 2011/0178389 A1* | 7/2011 | Kumar | A61B 8/12 600/411 |
| 2013/0329014 A1* | 12/2013 | Obata | H04N 5/23218 348/51 |
| 2015/0087958 A1* | 3/2015 | Kartman | A61B 6/037 600/411 |
| 2016/0247293 A1* | 8/2016 | Beylin | A61B 6/5264 |
| 2020/0170605 A1* | 6/2020 | Qi | A61B 6/037 |
| 2021/0213962 A1* | 7/2021 | Pishehvari | G01S 7/415 |

OTHER PUBLICATIONS

Zeraatkar, Navid, et al. "Compensation of Head Motion in AdaptiSPECT-C Using a GPU-Based Iterative Reconstruction Algorithm: Initial Results." 2019 IEEE Nuclear Science Symposium and Medical Imaging Conference (NSS/MIC). IEEE, 2019.

* cited by examiner

*Primary Examiner* — Amara Abdi (57) ABSTRACT

Systems and methods for imaging. An external device may be used to acquire optical image data of a subject. One or more physical parameters of the subject may be determined based on the optical image data. The one or more physical parameters may be translated to one or more properties of the subject. The one or more properties may then be used to generate medical image data of the subject.

20 Claims, 5 Drawing Sheets

EXTERNAL DEVICE-ENABLED IMAGING SUPPORT

TECHNICAL FIELD

The present disclosure generally relates to image processing, and more particularly to an external device-enabled imaging support.

BACKGROUND

The field of medical imaging has seen significant advances since the time X-rays were first used to determine anatomical abnormalities. Medical imaging hardware has progressed from modern machines, such as Magnetic Resonance (MR) imaging scanners, Computed Tomographic (CT) scanners and Positron Emission Tomographic (PET) scanners, to multimodality imaging systems such as PET-CT and PET-MRI systems.

Digital medical images are reconstructed using raw image data obtained from a medical imaging device such as, for example, a computerized axial tomography (CAT) scanner, magnetic resonance imaging (MRI), etc. Digital medical images are typically either a two-dimensional ("2D") image made of pixel elements, a three-dimensional ("3D") image made of volume elements ("voxels") or a four-dimensional ("4D") image made of dynamic elements ("doxels"). Such 2D, 3D or 4D images are processed using medical image recognition techniques to determine the presence of anatomical abnormalities or pathologies, such as cysts, tumors, polyps, etc.

In nuclear imaging (e.g., SPECT), a quantitative reconstruction of a tracer distribution requires attenuation correction. An attenuation map may be needed for attenuation correction. The attenuation map is typically acquired through a transmission scan using a computed tomography (CT) scanner. To provide an attenuation map from CT, the subject may need to be exposed to a radiation dose, which is undesirable because of the associated risks. Alternatively, some methods perform image reconstruction without an actual attenuation map acquired by CT to avoid subjecting the patient to additional radiation doses. Either a non-attenuated correction reconstruction is performed, or deep learning techniques are performed on a non-attenuated reconstruction to estimate the attenuation map. However, such techniques either produce lower quality reconstructed image data and/or require extensive computing resources.

Another issue that needs to be addressed is associated with patient motion during image acquisition. Patients usually move during image acquisition, either involuntarily (e.g., breathing, sneezing, shaking) or voluntarily (e.g., talking, scratching). Such motion has an effect on image quality of reconstructed image data, especially on small details, such as those present in brain scans or lymph nodes. To correct for motion, a data-driven approach may be used. Data-driven models analyze the acquired projection data to identify motion fields present in the projection data. Motion correction and image reconstruction may then be performed using the identified motion fields.

SUMMARY

Described herein are systems and methods for imaging. An external device may be used to acquire optical image data of a subject. One or more physical parameters of the subject may be determined based on the optical image data. The one or more physical parameters may be translated to one or more properties of the subject. The one or more properties may then be used to generate medical image data of the subject.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of an interventional or therapeutic procedure, which may include times when the radiation source is either on or off. From time to time, for convenience of description, CT imaging data (e.g., cone-beam CT imaging data) may be used herein as an exemplary imaging modality. It will be appreciated, however, that data from any type of imaging modality including but not limited to x-ray radiographs, MRI (magnetic resonance imaging), PET (positron emission tomography), PET-CT (computed tomography), SPECT (single photon emission computed tomography), SPECT-CT, MR-PET, 3D ultrasound images or the like may also be used in various implementations.

Unless stated otherwise as apparent from the following discussion, it will be appreciated that terms such as "segmenting," "generating," "registering," "determining," "aligning," "positioning," "processing," "computing," "selecting," "estimating," "detecting," "tracking," or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present framework are not described with reference to any particular programming language. It will be appreciated that a variety of programming languages may be used.

As used herein, the term "image" refers to multi-dimensional data composed of discrete image elements (e.g., pixels for 2D images, voxels for 3D images, doxels for 4D datasets). The image may be, for example, a medical image of a subject collected by CT (computed tomography), MRI (magnetic resonance imaging), ultrasound, or any other medical imaging system known to one of ordinary skill in the art. The image may also be provided from non-medical contexts, such as, for example, remote sensing systems, electron microscopy, etc. Although an image can be thought of as a function from $R^3$ to R, or a mapping to $R^3$, the present methods are not limited to such images, and can be applied to images of any dimension, e.g., a 2D picture, 3D volume or 4D dataset. For a 2- or 3-Dimensional image, the domain of the image is typically a 2- or 3-Dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

The terms "pixels" for picture elements, conventionally used with respect to 2D imaging and image display, "voxels" for volume image elements, often used with respect to 3D imaging, and "doxels" for 4D datasets can be used interchangeably. It should be noted that the 3D volume image is itself synthesized from images obtained as pixels on a 2D sensor array and displays as a 2D image from some angle of view. Thus, 2D image processing and image analysis techniques can be applied to the 3D volume images. In the description that follows, techniques described as operating upon doxels may alternately be described as operating upon the 3D voxel data that is stored and represented in the form of 2D pixel data for display. In the same way, techniques that operate upon voxel data can also be described as operating upon pixels. In the following description, the variable x is used to indicate a subject image element at a particular spatial location or, alternately considered, a subject pixel. The terms "subject pixel", "subject voxel" and "subject doxel" are used to indicate a particular image element as it is operated upon using techniques described herein.

One aspect of the present framework uses an external device to estimate properties (e.g., attenuation map, motion data) of a subject without performing a medical imaging scan (e.g., CT or MR scan). The external device may be, for example, a handheld device or any other device with an optical camera that is external to the medical imaging device. The external device may be used to visually scan and generate an optical image of a subject before, during and/or after a medical imaging scan. The color information (e.g., picture) and/or depth information (e.g., point cloud) in the optical image may then be used to estimate the physical parameters (e.g., size, shape, position) of the subject and determine properties (e.g., attenuation map) for that patient. The framework advantageously enables attenuation correction to be performed for image reconstruction without having to perform a medical imaging scan, thereby minimizing radiation exposure and dose for the patient. Additionally, this is particularly advantageous to smaller clinical offices with a more portable set-up without access to a CT or MR scanner for performing attenuation correction.

Additionally, the relative position of the subject may be used to perform registration even before medical image acquisition is started. Unlike conventional techniques where registration can only be performed only after reconstruction, the present framework is able to perform registration before acquisition of the reference image even starts. A pre-acquisition registration speeds up the image reconstruction process because it does not require a registration step as the reconstructed image data is already properly registered. Additionally, a real-time display of the reconstructed image data may be provided to enable vision augmentation. By matching the subject's body position to the attenuation map, the subject is no longer required to be in the same position (e.g., lying on the bed) as when the reference image was acquired, but can be, for example, sitting on a chair or standing up. This approach may advantageously be used where the attenuation map is acquired from the subject in one position and the reference image is acquired from the subject in another position. The workflow of multiple scans, particularly on patients undergoing theranostics, is advantageously improved since multiple scans may be performed using the same or different imaging systems at different time points without requiring the same position for all the scans.

Yet another aspect of the present framework uses video image data recorded by the external device during medical imaging to monitor, detect and correct for patient motion. This approach uses the external device as a source of information, which makes it easily replaceable. Furthermore, since each scan or subject is different, motion registration may guide the technician to the area they should monitor. These and other exemplary features and advantages will be described in more details herein.

Figure 1:
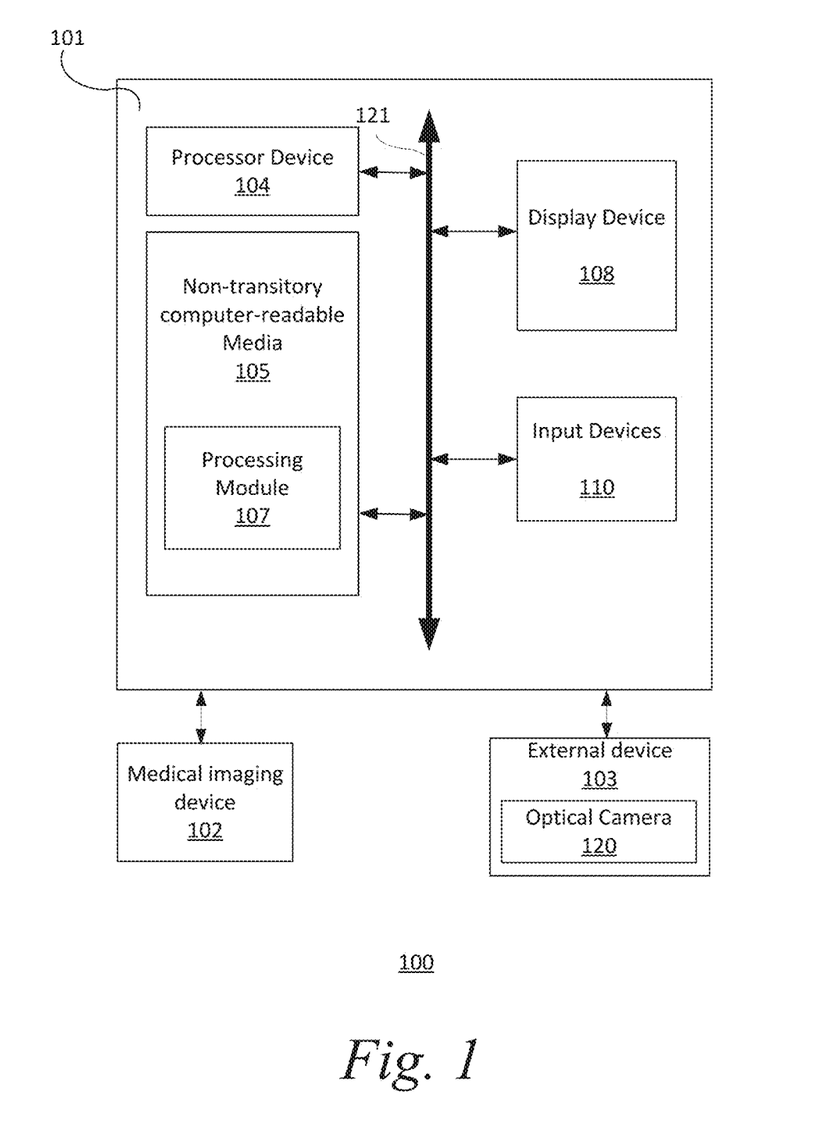
FIG. 1 is a block diagram illustrating an exemplary system.

FIG. 1 is a block diagram illustrating an exemplary system 100. The system 100 includes a computer system 101 for implementing the framework as described herein. Computer system 101 may be a desktop personal computer, a portable laptop computer, another portable device, a mini-computer, a mainframe computer, a server, a cloud infrastructure, a storage system, a dedicated digital appliance, a communication device, or another device having a storage sub-system configured to store a collection of digital data items. In other implementations, computer system 101 is connected (e.g., using a network) to other machines, such as medical imaging device 102 and external device 103. In a network deployment, computer system 101 may operate in the capacity of a server, a client user machine in server-client user network environment, or as a peer machine in a peer-to-peer (or distributed) network environment.

Computer system 101 may include a processor device or central processing unit (CPU) 104 coupled to one or more non-transitory computer-readable media 105 (e.g., computer storage or memory), a display device 108 (e.g., monitor) and various input devices 110 (e.g., mouse, touchscreen, keyboard) via an input-output interface 121. Computer system 101 may further include support circuits such as a cache, a power supply, clock circuits and a communications bus. Various other peripheral devices, such as additional data storage devices and printing devices, may also be connected to the computer system 101.

The present technology may be implemented in various forms of hardware, software, firmware, special purpose processors, or a combination thereof, either as part of the microinstruction code or as part of an application program or software product, or a combination thereof, which is executed via the operating system. In one implementation, the techniques described herein are implemented as computer-readable program code tangibly embodied in one or more non-transitory computer-readable media 105. In particular, the present techniques may be implemented by a processing module 107. Non-transitory computer-readable media 105 may include random access memory (RAM), read-only memory (ROM), magnetic floppy disk, flash memory, and other types of memories, or a combination thereof. The computer-readable program code is executed by processor device 104 to process images acquired by, for example, a medical imaging device 102. As such, the computer system 101 is a general-purpose computer system that becomes a specific purpose computer system when executing the computer-readable program code. The computer-readable program code is not intended to be limited to any particular programming language and implementation thereof. It will be appreciated that a variety of programming languages and coding thereof may be used to implement the teachings of the disclosure contained herein.

The same or different computer-readable media 105 may be used for storing image sets, patient records, knowledge base, and so forth. Such data may also be stored in external storage or other memories. The external storage may be implemented using a database management system (DBMS) managed by the processor device 104 and residing on a memory, such as a hard disk, RAM, or removable media. The external storage may be implemented on one or more additional computer systems. For example, the external storage may include a data warehouse system residing on a separate computer system, a picture archiving and communication system (PACS), or any other now known or later developed hospital, medical institution, medical office, testing facility, pharmacy or other medical patient record storage system.

The medical imaging device 102 is a radiological imaging device that acquires medical image data that reveals internal structures hidden by skin and bones of the subject. Such medical imaging device 102 may use technologies of X-ray radiography, computed tomography (CT), magnetic resonance (MR) imaging, ultrasound, endoscopy, elastography, tactile imaging, thermography, medical photography, nuclear medicine functional imaging techniques (e.g., positron emission tomography (PET), single-photon emission computed tomography (SPECT)), or a combination thereof.

The external device 103 is external to the medical imaging device 102. The external device 103 may be a smartphone, a laptop, a handheld device, or any other computing device with an optical camera 120. The external device 103 may include a processor device, non-transitory computer readable media and appropriate peripherals, such as a keyboard, touchscreen and/or a display device, and can be operated in conjunction with the entire system 100. For example, the external device 103 may communicate with the medical imaging device 102 so that the image data collected by the medical imaging device 102 can be rendered and viewed at the external device 103. The optical camera 120 is integrated, or connected, to the external device 103, and is used to record optical image data using visible, ultraviolet and/or infrared light. The optical camera 120 may be a red-green-blue (RGB) camera, a three-dimensional camera, a depth camera, a time-of-flight camera, or a combination thereof. The external device 103 may communicate directly with the computer system 101 to display processed images and/or output image processing results. The external device 103 may include a graphical user interface to provide optical image capture guidance and receive user input.

It is to be further understood that, because some of the constituent system components and method steps depicted in the accompanying figures can be implemented in software, the actual connections between the systems components (or the process steps) may differ depending upon the manner in which the present framework is programmed. Given the teachings provided herein, one of ordinary skill in the related art will be able to contemplate these and similar implementations or configurations of the present framework.

Figure 2:
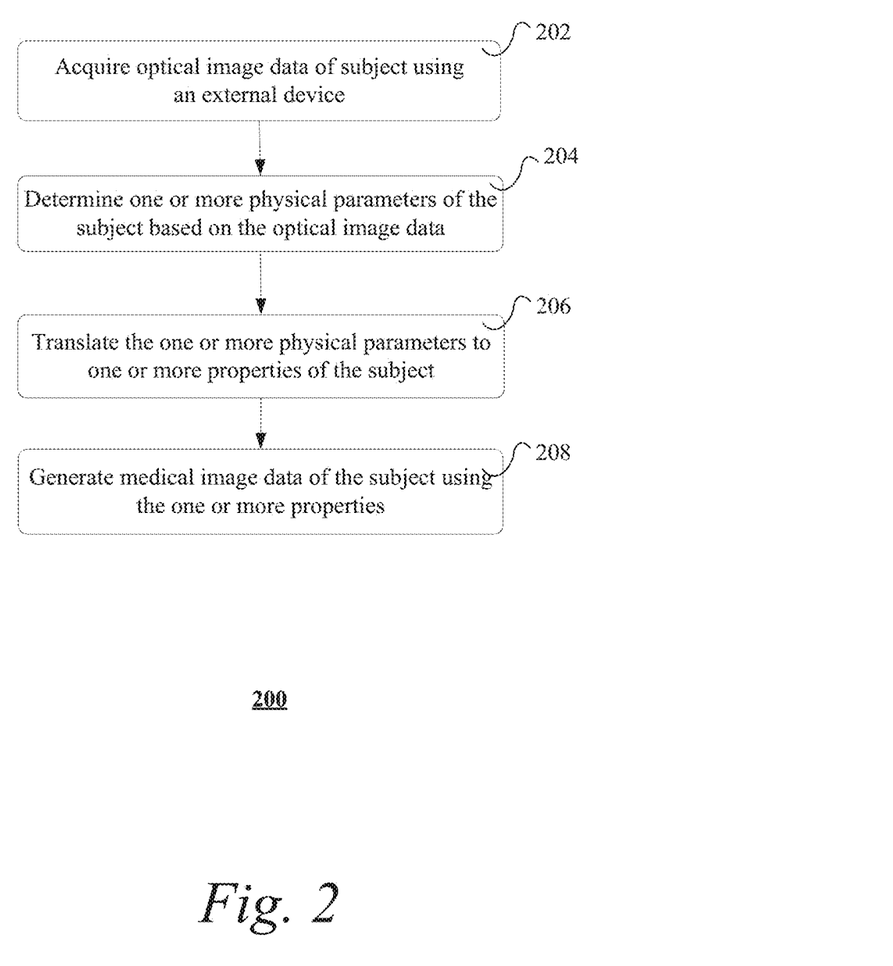
FIG. 2 shows an exemplary imaging method.

FIG. 2 shows an exemplary imaging method 200. It should be understood that the steps of the method 200 may be performed in the order shown or a different order. Additional, different, or fewer steps may also be provided. Further, the method 200 may be implemented with the system 100 of FIG. 1, a different system, or a combination thereof.

At 202, external device 103 is used to acquire optical image data of a subject. The external device 103 is external to the medical imaging device 102 and may be, for example, a handheld device (e.g., smartphone) with an optical camera 120. By using an external device 103 instead of one that is integrated within the medical imaging device 102 to obtain the optical image data, the likelihood of failure is advantageously decreased since it is easily replaceable with another external device when it is faulty and additional external devices are likely to be widely available in the hospital or clinical center. Furthermore, instead of relying on the medical imaging device head to acquire required angles, a user interface screen displayed on external device 103 may provide guidance as to the locations, angles and/or positions that need to be visually scanned by the optical camera 120 to generate the optical image data.

The optical image data of the subject may be static or dynamic (e.g., video). The optical image data may be recorded by the optical camera 120 of the external device 103 using visible, ultraviolet and/or infrared light. The optical camera 120 may be, for instance, a red-green-blue (RGB) camera, a three-dimensional camera, a depth camera, a time-of-flight camera, a radar camera, a visible structured-light 3D scanner, or a combination thereof. Additional patient-specific knowledge may be provided via the external device 103. For example, a user interface screen may be displayed on the external device 103 to provide a series of questions to be answered by the user, such as weight, gender, situs inversus, implants, etc. Alternatively, such knowledge may be extracted from the medical record of the subject.

In some implementations, the optical image data is acquired before, during and/or after the medical imaging scan of the subject begins to acquire raw image data. For example, prior to the scan, while the subject is lying on the bed of the medical image scanner, a technician or other medical personnel may hold the external device 103 and take an optical image or video of the subject from different angles. The subject advantageously does not need to be in the same position or pose as during the medical imaging scan.

Figure 3:
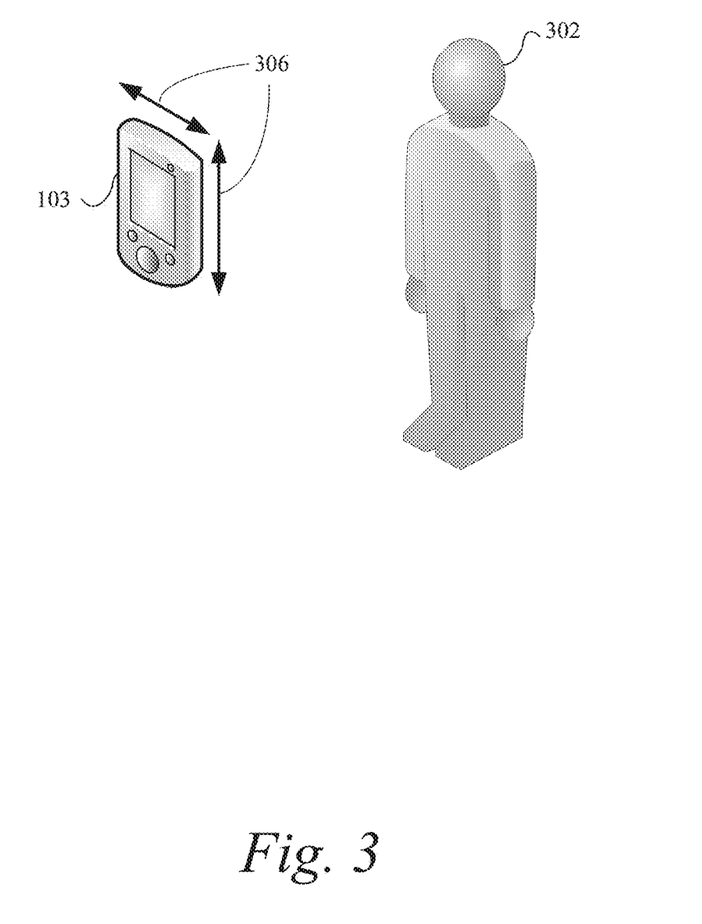
FIG. 3 shows an exemplary position of the subject.

FIG. 3 shows an exemplary position of the subject 302. Although the subject 302 is shown to be standing up, he or she can also engage in other poses (e.g., sitting down). The subject 302 may be in, for example, the physician's office where no medical image scanner (e.g., CT, MR) or a different medical image scanner is available. To acquire the optical image data, the physician or other user may move the handheld external device 103 in different directions 306 (e.g., up-down, left-right) to record optical images of the subject 302 from different angles. For example, the physician may move the handheld external device 103 to acquire optical images from one side of the bed for half of the medical imaging scan, and then move to the other side of the bed while acquiring additional optical images, covering, for example, 10-20 degrees at each stage. It should be appreciated that the angles may vary depending on the application or scan.

Returning to FIG. 2, at 204, processing module 107 receives the optical image data and determines one or more physical parameters of the subject based on the optical image data. The one or more physical parameters describe physical characteristics of the subject, and may include, for instance, size, shape of the subject's body or body part, locations of landmarks on the subject, or a combination thereof. The shape of the subject's body, for example, is defined by the skeletal structure and distribution of muscles and fat. The shape of the subject's body may be classified based on, for example, a bust-waist-hip circumference ratio. Exemplary shapes include, but are not limited to, V, hourglass, apple, pear, spoon, bell, rectangle, straight, banana, and so forth. The shape of the body part may be used to automatically identify the body part (e.g., head, arm, leg, torso) and their sizes based on the optical image data. A landmark is a point of interest that defines what is important and distinctive in an image (e.g., joints of the body).

Various methods may be used to determine the one or more physical parameters based on the optical image data. In some implementations, a learning-based method (e.g., deep learning) is applied to map human pixels of the optical image data (e.g., RGB data) to a 3D surface of the body or body part of the subject. The one or more physical parameters may then be determined using the 3D surface. An exemplary learning-based method using convolutional neural networks is described in Güler, Riza Alp et al., *DensePose: Dense Human Pose Estimation in the Wild*, 2018 IEEE/CVF Conference on Computer Vision and Pattern Recognition (2018): 7297-7306, which is herein incorporated by reference. Other methods for determining physical parameters, including non-learning-based methods and those based on other types of image data (e.g., depth images, RGB/depth images), are also useful. For example, some methods estimate the shape from depth images by fitting a deformable human model to the input depth map with iterative optimization.

At 206, processing module 107 translates the one or more physical parameters to one or more properties of the subject. The one or more properties may include an attenuation map, target image (e.g., attenuation map) registered to a reference image, motion data, etc. By estimating the one or more properties from the one or more physical parameters derived from the optical image data, the subject is advantageously not subjected to further radiation like in conventional techniques.

In some implementations, processing module 107 estimates an attenuation map based on the shape of the subject's body or body part. An attenuation map represents the spatial distribution of linear attenuation coefficients for the region of the subject's anatomy that is included in the medical imaging study. Using the shape derived from the optical image data, the body part may first be identified. Exemplary body parts include, for example, head, arm, hand, leg, torso, etc. An attenuation map may then be fitted to the body part or body by, for example, using a machine-learning algorithm.

The attenuation map may be determined by looking up a dictionary (or database) of pre-generated attenuation maps using the shape of the body part or body. The attenuation maps in the dictionary may be pre-generated by, for example, employing X-ray computed tomography (CT), magnetic resonance or nuclear imaging (e.g., PET) techniques. A CT-based attenuation map, for example, represents the tissue-density distribution across the imaging volume. Other types of attenuation maps generated using other techniques are also useful. Since different body parts are associated with different attenuation maps, the dictionary may map different body parts to different attenuation maps. Additionally, since the shape of the body is determined by fat and muscle distribution, which is in turn associated with the attenuation coefficients, the dictionary may map different shapes (e.g., V, hourglass, apple, pear, spoon, bell, rectangle, straight, banana) of the same body part to different attenuation maps.

In some implementations, processing module 107 registers a target image to a reference image by using the locations of landmarks (or features) extracted from the optical image data to align the target image to the reference image. The goal of the registration is to align the corresponding landmarks (or features) in the target image with respect to the reference image. The registration may include rigid or non-rigid (or elastic) transformations. The target and reference images may be, for example, attenuation maps estimated using optical image data, as previously described. Alternatively, the target and reference images may also be attenuation maps constructed directly from a CT, MR or a nuclear scan (e.g., PET) without the use of optical image data. The registration may be performed dynamically to register attenuation maps over time. More particularly, given the optical image data at current time point $t_i$ and the attenuation map at previous time point $t_{i-1}$, the processing module 107 may estimate the attenuation map at current time point $t_i$.

Figure 4A:
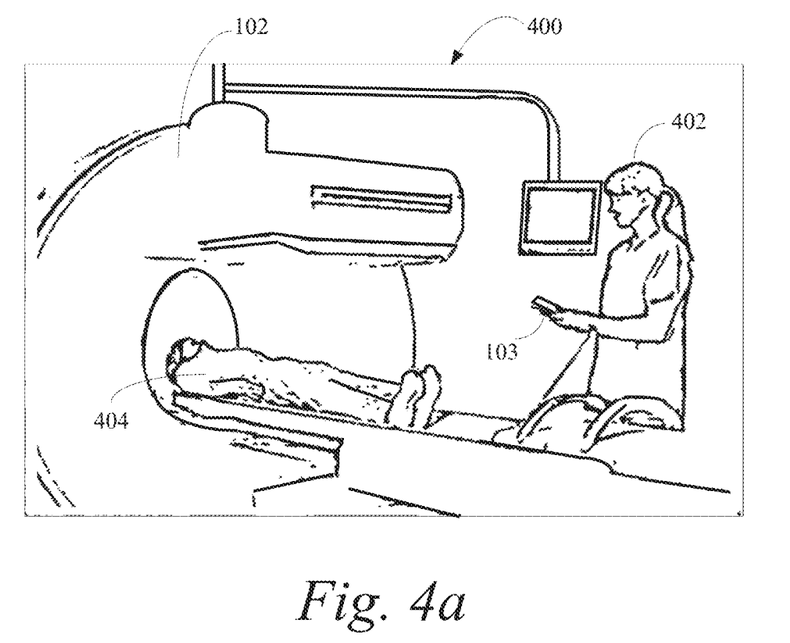
FIG. 4a shows an exemplary system for attenuation registration.
Figure 4B:
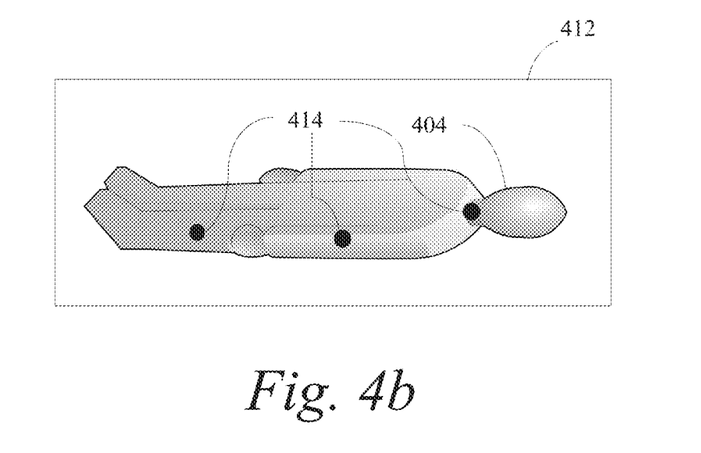
FIG. 4b shows an exemplary optical image of the subject recorded by the external device.

FIG. 4a shows an exemplary system 400 for attenuation registration. Prior to the scan of the subject 404 using the medical imaging device 102, the technician 402 may stand next to the scan bed and hold the external device 103 to register the relative position of the subject 404 to the medical imaging device 102. FIG. 4b shows an exemplary optical image 412 of the subject 404 recorded by the external device 103. The joints 414 of the subject 404 may be detected in the optical image 412 as landmarks for the registration.

In other implementations, processing module 107 estimates motion data by using one or more locations of landmarks (or features) extracted from the optical image data. The motion data may be represented by, for example, six degrees of motion as rotation and/or displacement along the X, Y and Z axes relative to the initial position of each landmark. Other types of representation, such as motion vectors, are also possible.

Figure 5A:
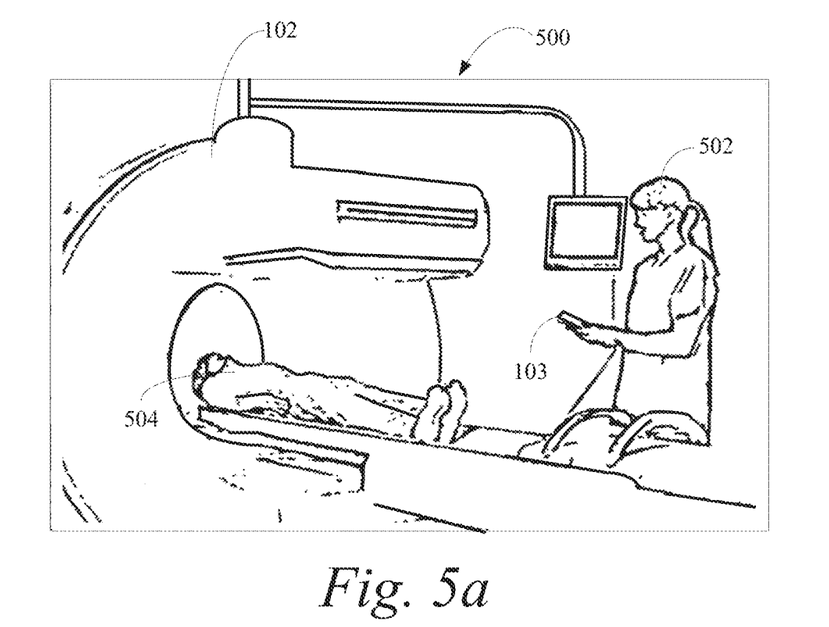
FIG. 5a shows an exemplary system for motion tracking.
Figure 5B:
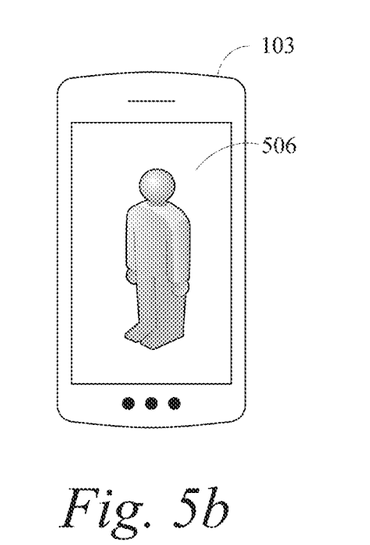
FIG. 5b shows an exemplary user interface screen on external device.

FIG. 5a shows an exemplary system 500 for motion tracking. During the scan of the subject 504 using the medical imaging device 102, the technician 502 may stand next to the scan bed and hold the external device 103 to track the motion of the subject 504. Different types of motion, such as rigid body (e.g., head motion) or non-rigid (or elastic) body motion (e.g., respiratory motion), may be tracked. FIG. 5b shows an exemplary user interface screen 506 on external device 103. Since each scan and patient is different, the user interface screen 506 may guide the technician 502 to the location of motion where they need to monitor so as to measure motion more accurately.

Returning to FIG. 2, at 208, the one or more properties are used to generate medical image data of the subject. Raw image data may first be acquired by performing a medical imaging scan using the medical imaging device 102. Medical image data may then be reconstructed using the raw image data.

In some implementations, the attenuation map estimated in the previous step 206 is used to determine the optimal dose of a radiopharmaceutical to be administered to (e.g., injected) the subject for performing a nuclear image acquisition. A radiopharmaceutical may include a radioisotope (or radiotracer) that emits penetrating gamma rays used for imaging, where the radiation has to escape the body before being detected by a nuclear medical imaging device (e.g., SPECT, PET scanner). Exemplary isotopes include, but are not limited to, 99mTc, I-123, I-131, Tl201, In111 and F18. The optimal radiopharmaceutical dose to be administered to the patient may depend on the specific patient attenuation characteristics and specific diagnostic task. For example, larger patients with higher body mass index (BMI) may require a larger radiopharmaceutical dose than a smaller patient because the radiation has to pass through more fat tissue. Different people with same body mass index (BMI) but different body types or shapes may also need different doses of radiopharmaceutical to achieve the same image quality. A lookup table may be used to map the attenuation coefficients in the estimated attenuation map to the radiopharmaceutical dose. Other methods may also be used to optimize the radiopharmaceutical dose.

Processing module 107 may reconstruct medical image data based on the raw image data and the one or more properties. In some implementations, the medical image data is reconstructed using the attenuation map estimated in step 206 to correct for attenuation. Attenuation is the loss of detection of true coincidence events because of the absorption or scatter of photons emitted from radiotracers in the body. The estimated attenuation map may be used to correct the emission data for errors contributed by photon attenuation. The attenuation correction process may be applied before or after image reconstruction, or during image reconstruction (e.g., integrated within the transition matrix of an iterative reconstruction algorithm). Other methods are also useful.

In other implementations, the medical image data is reconstructed with motion correction using the motion data derived in previous step 206. Motion correction may be applied before or after image reconstruction. Alternatively, motion correction may be integrated within the reconstruction algorithm (e.g., maximum likelihood expectation-maximization).

While the present framework has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. An imaging method, comprising:
acquiring, by a device external to a medical imaging device, optical image data of a subject;
determining one or more physical parameters of the subject based on the optical image data, wherein the one or more physical parameters of the subject include locations of landmarks on the subject extracted from the optical image data of the subject;
translating the one or more physical parameters to one or more properties of the subject; and
generating medical image data of the subject using the one or more properties.

2. The method of claim 1 wherein acquiring the optical image data comprises visually scanning the subject from different angles using a handheld device.

3. The method of claim 1 wherein acquiring the optical image data comprises recording a video of the subject.

4. The method of claim 1 wherein acquiring the optical image data comprises acquiring depth data, red-green-blue (RGB) data or a combination thereof.

5. The method of claim 1 wherein acquiring the optical image data comprises acquiring the optical image data before performing, by the medical imaging device, a medical imaging scan to acquire raw image data for generating the medical image data.

6. The method of claim 1 wherein determining the one or more physical parameters comprises determining a shape of a body or a body part of the subject.

7. The method of claim 6 wherein determining the shape comprises applying a learning-based method to map human pixels of the optical image data to a three-dimensional surface of the body or the body part of the subject.

8. The method of claim 6 wherein translating the one or more physical parameters to the one or more properties comprises translating the shape to an attenuation map.

9. The method of claim 8 wherein translating the shape to the attenuation map comprises looking up a dictionary of pre-generated maps using the shape.

10. The method of claim 1 wherein translating the one or more physical parameters to the one or more properties comprise translating the locations of the landmarks to a registered target image.

11. The method of claim 1 wherein translating the one or more physical parameters to the one or more properties comprises registering an attenuation map by using the locations of the landmarks on the subject.

12. The method of claim 11 wherein registering the attenuation map comprises dynamically registering the attenuation map over time.

13. The method of claim 1 wherein translating the one or more physical parameters to the one or more properties comprise translating the locations of the landmarks to motion data.

14. The method of claim 1 wherein generating the medical image data of the subject using the one or more properties comprises performing an acquisition, by the medical imaging device, of raw image data supported by the one or more properties.

15. The method of claim 14 wherein performing the acquisition of raw image data supported by the one or more properties comprises determining an optimal radiopharmaceutical dose to be administered to the subject for performing the acquisition.

16. The method of claim 1 wherein generating the medical image data of the subject using the one or more properties comprises reconstructing the medical image data using an estimated attenuation map to correct for attenuation.

17. The method of claim 1 wherein generating the medical image data of the subject using the one or more properties comprises reconstructing the medical image data using motion data to correct for motion.

18. An imaging system, comprising:
an external device with an optical camera that is external to a medical imaging device, wherein the external device acquires optical image data of a subject; and
a computer system coupled to the external device, the computer system includes
a non-transitory memory device for storing computer readable program code, and
a processor device in communication with the non-transitory memory device, the processor device being operative with the computer readable program code to perform steps including
determining one or more physical parameters of the subject based on the optical image data, wherein the one or more physical parameters of the subject include locations of landmarks on the subject extracted from the optical image data of the subject,
translating the one or more physical parameters to one or more properties of the subject, and
generating medical image data of the subject using the one or more properties.

19. The imaging system of claim 18 wherein the optical camera comprises a red-green-blue (RGB) camera, a three-dimensional camera, a depth camera, a time-of-flight camera, or a combination thereof.

20. One or more non-transitory computer-readable media embodying instructions executable by a machine to perform operations for imaging, comprising:
acquiring, by a device external to a medical imaging device, optical image data of a subject;
determining one or more physical parameters of the subject based on the optical image data, wherein the one or more physical parameters of the subject include locations of landmarks on the subject extracted from the optical image data of the subject;
estimating an attenuation map using the one or more physical parameters; and
generating medical image data of the subject using the attenuation map.

\* \* \* \* \*